United States Patent [19]

Witzel

[11] Patent Number: 5,769,809
[45] Date of Patent: Jun. 23, 1998

[54] BELOW THE JOINT AMPUTATION LIMB PROTECTOR APPARATUS

[76] Inventor: Marshall Witzel, 2445 Hybernia Dr., Highland Park, Ill. 60035

[21] Appl. No.: 611,100

[22] Filed: Mar. 5, 1996

[51] Int. Cl.$^6$ ........................................... A61F 5/00
[52] U.S. Cl. ................. 602/62; 602/26; 602/75; 623/32
[58] Field of Search ............... 2/24; 623/32, 33; 602/26, 62, 75–76

[56] References Cited

U.S. PATENT DOCUMENTS

| | | | |
|---|---|---|---|
| 3,670,339 | 6/1972 | Cooper et al. | 2/24 X |
| 4,024,584 | 5/1977 | Smith | 2/24 |
| 4,150,442 | 4/1979 | Boone | 2/24 |
| 4,674,489 | 6/1987 | Lundy | 602/76 |
| 4,822,371 | 4/1989 | Jolly | 623/32 |
| 5,031,240 | 7/1991 | Nierhaus | 602/26 |
| 5,258,037 | 11/1993 | Caspers | 623/33 |
| 5,306,229 | 4/1994 | Brandt et al. | 602/61 X |
| 5,554,105 | 9/1996 | Taylor | 602/26 |

FOREIGN PATENT DOCUMENTS 2607384  6/1988  France  ................ 602/26

Primary Examiner—Richard J. Apley
Assistant Examiner—Denise Pothier
Attorney, Agent, or Firm—Dick and Harris

[57] ABSTRACT

An apparatus for protecting the joint area of a limb, in particular wherein the limb has undergone an amputation below the joint, for example a below-the-knee amputation of a leg. A generally tubular member, preferably fabricated from a resiliently stretchable material is provided. The tubular member may have both ends open, or a lower end may be closed. At one or more of the ends, a cuff is provided. The protector apparatus is configured to have a progressively variable capacity for resilient stretching, which capacity varies along the length of the apparatus.

14 Claims, 2 Drawing Sheets

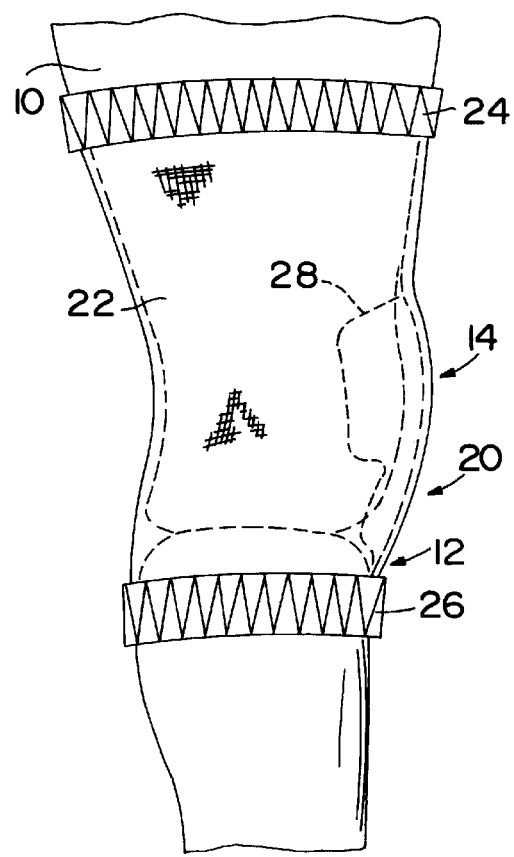
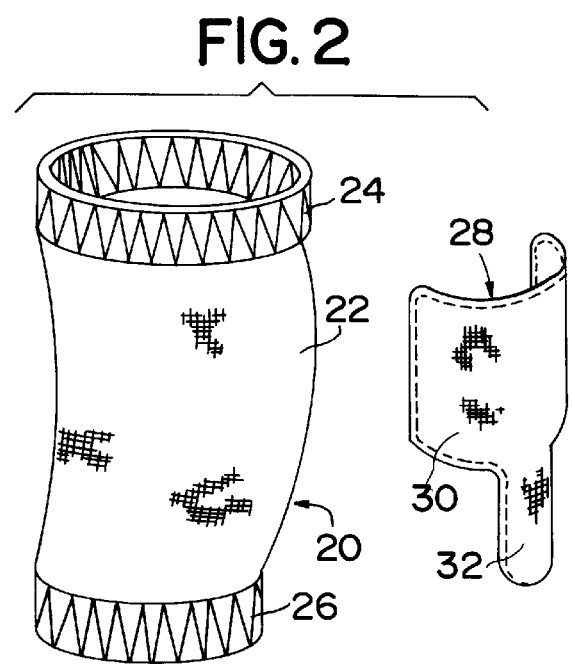

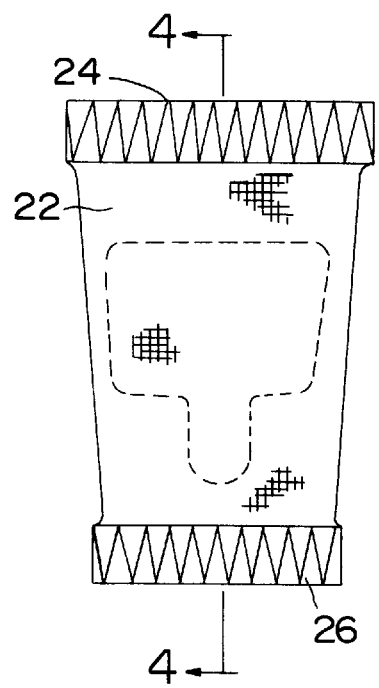
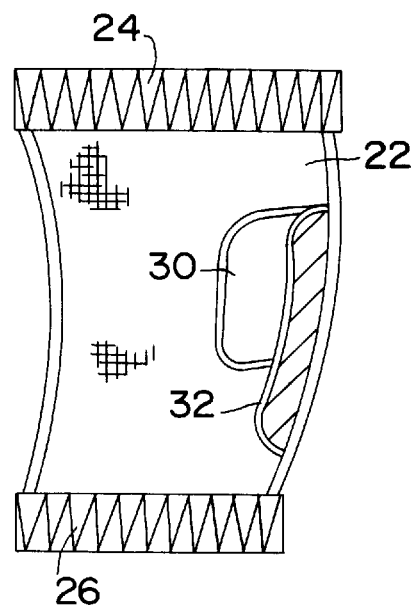
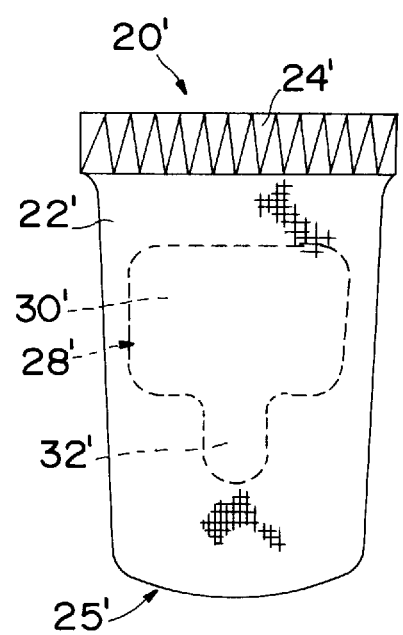

BELOW THE JOINT AMPUTATION LIMB PROTECTOR APPARATUS

BACKGROUND OF THE INVENTION

The present invention is directed to apparatus, typically in the form of either closed or open-ended hose, for the support of human limbs, and in particular to the support of limbs in regions where bending may take place, such as the knee or elbow, and especially in cases where an amputation of the limb below the joint has occurred.

Prior art hose devices for the protection or treatment of limbs are known. Such devices, as leg compression hose comprise an elongated tubular portion fabricated from some form of fabric material, such as terry cloth or the like. The tubular portion may have some form of slight bend formed therein, to more readily accommodate the heel, and provide a more contoured fit of the limb. Apart from the bend, the tubular portion typically has a generally constant diameter from one end to the other. The fabric of the tubular portion may be woven so as to accommodate a certain amount of stretching both along the axis of the limb and circumferentially, so that when a properly sized support is worn it will exert a slightly compressive force on the leg or other limb to which it is applied. Such slightly compressive force being believed to have at least some therapeutic affect.

Typically located at the extreme ends of the tubular portion are two cuffs. Such cuffs are typically formed from a fabric material which has been woven so as to accommodate stretching, but only in the circumferential direction around the cuff. Axial stretching, like that which is typically accommodated by the tubular portion, is typically neither provided nor desired. In addition, the cuffs are typically formed from a more reinforced material so as to provide strength and handling characteristics. Typically, the cuffs are of substantially the same diameter as their adjacent tubular portions. Further, the cuffs at the opposite ends of the support/protector typically have substantially the same dimensions (circumference, axial length, capacity for elasticity, etc).

Such support protector apparatus typically do not take into account the fact that human limbs, generally tend to have different circumferences, on opposite sides of a joint, while the cuffs and tubular portions generally have a more or less constant circumference. Accordingly, over time, due to the homogeneity of the capacity for stretching which is typical of such apparatus, the protector will become overly stretched at one end, loosing its capacity to return to normal shape when taken off, and further losing its capacity to exert the therapeutic compression force on the leg.

Other prior art apparatus for protecting limbs, such as heel or elbow protectors for decubitus ulcer treatment, such as those manufactured by Heelbo, Inc., typically comprise a relatively short tubular portion, typically only slightly longer than the outside distance around the joint to be protected. In addition, an insert pad which may be either removable or fixedly positioned along the interior of the tubular portion, so as to be positioned over the respective joint which is to be protected, may be provided. Typically such insert pads comprise a resiliently compressible member, such as urethane foam, which is then covered by a soft, durable, relatively non-stretchable fabric material. The pad thereafter may be affixed permanently to a specific interior location in the tubular portion, such as by stitching. Alternatively, the pad may be removably mounted on the interior of the tubular portion, such as through the use of hook and loop material, which is typically sold under the name VELCRO™. Such a removably affixed pad can be moved for specific desired positioning, or for separate cleaning or replacement purposes.

Such support/protection devices, as those which contain inserts, are, like the previously-described prior art protector devices, typically not configured to take into account variations in the circumferences of the various body portions being covered. Further, the insert pads which may typically be used with such apparatus likewise usually do not take into account the variations in the contours and sizes of the portions of the limb which are being protected.

Such potential drawbacks become particularly evident when such protector devices are used for the protection of a limb joint, wherein a portion of the limb has been amputated below the joint, for example a below-the-knee amputation of a leg. In such instances, the tissues surrounding such joints are frequently overly strained and particularly sensitive and may require additional facilitated protection on a day-to-day basis. In particular, when such a limb is fitted with a prosthetic such as an prosthetic lower leg, the fittings can produce additional strain stress and shock to the tissues of the joint and at the amputation site, further emphasizing the need for facilitated protection and support in those regions.

It would therefore be desirable to provide an improved limb joint support/protector apparatus which takes into account variations in limb circumference.

It would further be desirable to provide an improved protector apparatus for limb joints, which is particularly advantageously adapted for use on limbs, which have undergone a below-the-joint amputation.

These and other objects of the invention will become apparent in light of the present specification including claims and drawings.

SUMMARY OF THE INVENTION

The present invention is directed to a protector apparatus for the facilitated protection of a joint of a human limb, such as a knee. The protector apparatus comprises a substantially tubular portion operably configured to insertingly receive therethrough and thereafter substantially surround a portion of a human limb. The tubular portion has a first end for orientation above said joint and a second end for orientation below said joint, the tubular portion being open at least one of the first and second ends thereof. The tubular portion further has a longitudinal axis. The tubular portion further includes first means for enabling resilient stretching of the tubular portion, at least along a circumferential direction on the tubular portion about the longitudinal axis, from an original configuration to one or more stretched configurations, upon exertion of a stretching force on the tubular portion, the means for enabling resilient expansion of the tubular portion further being operably configured to promote circumferential stretching upon said exertion of a stretching force on said tubular portion, the amount of circumferential stretch proximate the first end of the tubular portion having a looser, less compressive degree of elasticity than the amount of circumferential stretch and associated degree of elasticity proximate to the second end of the tubular portion.

The invention further comprises cuff means, operably disposed substantially adjacent to at least one of the first and second ends of the tubular portion, and extending substantially about the respective end of the tubular portion, for facilitated reinforcement of the tubular portion in the regions thereof adjacent the respective end, while accommodating the differentiated degrees of circumferential elasticity between said first and second ends. In a preferred embodiment of the invention, the cuff means are disposed substantially adjacent an upper first end of the tubular portion, said cuff means possessing a circumferential elasticity no greater than that of the portion of the tubular portion proximate thereto. Also in a preferred embodiment of the invention, the cuff means are disposed substantially adjacent a lower second end of the tubular portion, said cuff means possessing a circumferential elasticity no less than that of the portion of the tubular portion proximate thereto.

Preferably, the cuff means are disposed substantially adjacent upper first and lower second ends of the tubular portion, respectively, said cuff means adjacent said upper first end possessing a circumferential elasticity no greater than that of the portion of the tubular portion proximate thereto, while said cuff means adjacent said lower second end possessing a circumferential elasticity no less than that of the portion of the tubular portion proximate thereto.

The invention further comprises cushioning insert means operably disposed along an interior surface of the tubular portion, for facilitated receipt and protection of an exterior surface of a joint of a limb. Preferably, the cushioning insert means comprises a substantially cup-shaped member operably configured to insertingly receive and further cushion a joint of a limb. The cushion means further preferably comprises an elongated tongue member, operably emanating downwardly from the cup-shaped member, and operably configured to extend from the cup-shaped member along at least a portion of the lower leg portion of the leg.

In an alternative embodiment of the invention, one end of the tubular portion is closed.

In a preferred embodiment of the invention, the first end of the tubular portion has a circumference, in a relaxed configuration, which is substantially greater that the circumference of the second end.

The means for enabling resilient expansion of the tubular portion are further preferably configured to permit stretching of the tubular portion in a direction substantially parallel to the longitudinal axis of the tubular portion, and operably configured to promote longitudinal stretching upon said exertion of a stretching force on said tubular portion, so that the amount of longitudinal stretch proximate the first end of the tubular portion having a looser, less compressive degree of elasticity than the amount of longitudinal stretch and associated degree of elasticity proximate to the second end of the tubular portion.

The tubular portion, in an alternative embodiment of the invention, includes a substantially bent portion disposed axially between the first and second ends.

In one embodiment of the invention, the tubular portion is configured to insertingly receive and surround the knee region of a leg. In another embodiment of the invention, the tubular portion is configured to insertingly receive and surround the elbow portion of an arm.

BRIEF DESCRIPTION OF THE DRAWINGS

FIG. 1 is a side elevation, of an improved limb protection apparatus, according to a preferred embodiment of the invention, in position on a human leg.

FIG. 2 is an exploded side perspective view of the apparatus, according to FIG. 1, showing the insert feature.

FIG. 3 is a perspective view of an insert apparatus which may be used as a part of the limb protector apparatus according to a preferred embodiment of the invention.

FIG. 4 is a side elevation, in section, of the limb protector apparatus of FIG. 3, as seen along lines 4—4.

FIG. 5 is a front elevation of an limb protector apparatus according to an alternative embodiment, in which one end of the apparatus is closed.

DETAILED DESCRIPTION OF THE DRAWINGS

While this invention is susceptible of embodiment in many different forms, there are shown in the drawings and will be described herein in detail, several preferred embodiments, with the understanding that the present disclosure is to be considered as an exemplification of the principles of the invention, and is not intended to limit the invention to the embodiments illustrated.

FIGS. 1–4 illustrate a protector apparatus 20 according to a preferred embodiment of the present invention, shown in place on a human leg 10. Leg 10 has undergone an amputation procedure, and the site of the amputation is indicated generally by reference numeral 12. The knee cap area is indicated generally by reference numeral 14.

Protector apparatus 20 comprises a generally tubular portion 22, upper cuff 24, lower cuff 26, and knee protector insert 28. Since knee insert 28 is positioned on the inside surface of tubular portion 22, insert 28 is illustrated with phantom lines. In a preferred embodiment of the invention, tubular portion 22 may be typically preferably configured to have a slightly bent appearance, even when not being worn, so as to more appropriately conform to the configuration of the knee region, both when the leg is straightened, bent, or in motion there between. Typically, the tubular portion 22 of protector apparatus 20, will have a somewhat conical configuration, having an upper end circumference (for accommodating an upper leg or upper arm) which is substantially greater than the lower end circumference (for the lower leg or arm), with the circumference varying in between in any manner as deemed appropriate, although a linear variation may be preferred. Such a generally conical configuration will assist in the apparatus' ability to conform more readily to the varying contours of a typical limb in a joint region, without excess strain to the apparatus, unnecessary discomfort to the wearer, etc. Accordingly, even when apparatus 20 is not being worn, cuff 24 will have a greater circumference than lower cuff 26. However, both cuffs 24 and 26 will have unstressed circumferences which are substantially less than the circumferences of those portions of the limb and/or prosthesis around which the respective cuffs will be placed on an intended wearer.

In a preferred embodiment of the invention, the relative capacities for stretching of cuffs 24 and 26 will be configured so that the variations in circumference of the tubular portions which the respective cuffs 24 and 26 will surround will be taken into account. Specifically, the relative resting circumferences of cuffs 24 and 26, and the construction thereof so as to provide resilient stretching capacity, will be configured so that when cuff 24 is stretched a total distance which is twice the circumference of cuff 26, when stretched, the circumferential tension force exerted by cuff 24 will be the same as the circumferential tension force exerted by cuff 26. By increasing the amount of strain (in terms of percentage change in length) that cuff 24 can undergo, the amount of force exerted upon the wearer is lessened, thus reducing damage to the protector apparatus and reducing the potential for discomfort and/or actual injury to the wearer, which could be caused from prolonged wearing of such a protector apparatus.

That is, cuff 24 possesses a circumferential elasticity no less than that of the portion of the tubular portion proximate thereto, while cuff 26, if present, possesses a circumferential elasticity no greater than that of the portion of the tubular portion proximate thereto.

In the preferred embodiment of the invention, the ability of the cuff to stretch (at least circumferentially) and capacity to subsequently return to an original smaller configuration, once stress has been removed from the apparatus, is accomplished not by the placement of elastic material, such as rubber, into the cuffs, but rather through known techniques of imparting resilient stretching capacity into the fabric itself as a result of the weave. Accordingly, by providing somewhat additional material and looser weave into the construction of cuff 24, a greater amount of strain (percentage increase in dimension) can be accommodated with reduced stress (i.e., the pulling force) exerted on the wearer.

In addition to having a differential between the amounts of strain which the upper cuff 24 and lower cuff 26 can undergo relative to one another, the tubular portion 22, in a preferred embodiment of the invention, is likewise configured to be able to undergo differentiated stretching, in at least the circumferential direction. That is, the amount of circumferential stretch proximate the top, first end of the tubular portion has a looser, less compressive degree of elasticity than the amount of circumferential stretch and associated degree of elasticity proximate to the lower, second end of the tubular portion. Accordingly, the material of the tubular portion will be capable of stretching farther under the same amount of force, near upper cuff 24, than those regions of tubular portion 22 which are in the vicinity of lower cuff 26. This differentiated stretching can also be provided in the longitudinal direction.

Again, since in a preferred embodiment of the invention, no separate elastic members (such as rubber members, etc.) are provided, the variation in ability to stretch is provided in the tubular portion 22 by varying the tightness of the weave as well as the amount of material (in terms of thread length), which is provided in the respective regions of the tubular portion. For example, near upper cuff 24, the material in tubular portion 22 has a less tight weave but may also have more actual material in terms of thread length, which is more loosely coiled so as to permit greater amounts of stretching upon exertion of force.

The variation in stretching capacity of the tubular portion, as already stated will vary in a decreasing manner when proceeding from the upper cuff to the lower cuff. Near the region of the upper cuff 24, the capacity to stretch of the tubular portion will be less than or equal to that of the upper cuff 24, while the capacity to stretch in the vicinity of the lower cuff 26 will be equal to or greater than that of the lower cuff 26 itself. Again, such variation in the capacity to stretch can be accomplished utilizing known weaving techniques.

Although the protector apparatus, as so far described, can be utilized to the benefit of the wearer, in a preferred embodiment of the invention, a padded insert 28 will be provided, as illustrated in FIGS. 1, 2, 3 and 4. Insert 28 typically will be configured, as previously stated, as having a resilient padding member, such as urethane foam, surrounded by somewhat less resilient or even non-stretchable fabric material, such as nylon or the like. However, unlike prior art inserts which have been known in prior art protector apparatus, insert 28 will comprise two portions: a main body portion 30 and a downwardly extending tongue 32. Insert 28 additionally will typically be configured to have a normally curved or cup-like configuration, for conforming to the upper and outer surfaces of a knee cap region of a wearer's leg. Tongue 32, when positioned properly will extend downward below the knee cap toward and along the front of the lower leg. According to one preferred embodiment of the invention, insert 28 may be affixed to the interior surface of tubular portion 22, such as by the appropriate placement of stitching at the top center of main body portion 30 and at the lower end of tongue 32, for example. Insert 28 may be otherwise affixed at other location around its Periphery. Alternatively, insert 28 may be removably affixed to an inner surface of tubular portion 22, through the use of hook and loop material, such as VELCRO™ (not shown). The downwardly extending tongue 32 is particularly usefully in the embodiment of the protector for an individual having had a below knee amputation, since the tongue helps protect the front surface of the leg where the leg may join-up with the prosthesis, thus providing additional protection for the particularly sensitive area at the end of the limb where the limb joins the prosthesis.

An alternative embodiment of the invention is illustrated in FIG. 5, in which the support apparatus is configured to be worn in the absence of a prosthesis. Accordingly, only a upper cuff 24' is provided on apparatus 20'. At the opposite end of tubular portion 22', lower end 25 is closed, so that apparatus 20' is in the general form of a sock-like structure. Again, the elasticity at least in the direction, of tubular portion 22' will vary along the longitudinal direction, such that the region of tubular portion 22' which is in the vicinity of upper cuff 24', will permit a greater amount of stretching for the same amount of circumferential force, than will the region of tubular portion 22 which is in the vicinity of the closed end 25. Again, an insert 28', having a main body portion 30' and a tongue 32' may be provided.

The foregoing description and drawings merely serve to illustrate the invention and the invention is not limited thereto accept insofar as the appended claims are so limited, as those skilled in the art to have the disclosure before them will be able to make modifications and variations therein without departing from the scope of the invention.

What is claimed is:

1. A protector apparatus for the facilitated protection of a joint of a human limb, the protector apparatus comprising:

a substantially tubular portion operably configured to insertingly receive therethrough and thereafter substantially surround a portion of a human limb, the tubular portion having a first end for orientation of the joint and a second end for orientation below the joint, the tubular portion being open at the first and second ends thereof, the tubular portion having a longitudinal axis;

the tubular portion further including means for enabling resilient stretching of the tubular portion, at least along a circumferential direction on the tubular portion about the longitudinal axis, from an original configuration to one or more stretched configurations, upon exertion of a stretching force on the tubular portion, the means for enabling resilient expansion of the tubular portion further being operably configured to promote circumferential stretching upon said exertion of a stretching force on said tubular portion, the amount of circumferential stretch proximate the first end of the tubular portion having a looser, less compressive degree of elasticity than the amount of circumferential stretch and associated degree of elasticity proximate to the second end of the tubular portion, and cuff means, operably disposed substantially adjacent said first and second ends of the tubular portion, and extending substantially about the respective end of the substantially adjacent tubular portion for facilitated reinforcement of the tubular portion in the regions thereof adjacent the respective end, while accommodating the differentiated degrees of circumferential elasticity between said first and second ends and wherein said cuff means are disposed, in part, substantially adjacent an upper, first end of the tubular portion, said cuff means thereat possessing a circumferential elasticity no less than that of the portion of the tubular portion proximate thereto, wherein said cuff means are further disposed, in part, substantially adjacent a lower, second end of the tubular portion, said cuff means thereat possessing a circumferential elasticity no greater than that of the portion of the tubular portion proximate thereto.

2. The apparatus according to claim 1, wherein the cuff means are disposed substantially adjacent upper first and lower second ends of the tubular portion, respectively, said cuff means adjacent said upper first end possessing a circumferential elasticity no greater than that of the portion of the tubular portion proximate thereto, while said cuff means adjacent said lower second end possessing a circumferential elasticity no less than that of the portion of the tubular portion proximate thereto.

3. The apparatus according to claim 1 wherein the invention further comprises cushioning insert means operably disposed along an interior surface of the tubular portion, for facilitated receipt and protection of an exterior surface of a joint of a limb.

4. The apparatus according to claim 3, wherein the cushioning insert means comprises a substantially cup-shaped member operably configured to insertingly receive and further cushion a joint of a limb.

5. The apparatus according to claim 4, wherein the cushion means further comprises an elongated tongue member, operably emanating downwardly from the cup-shaped member, and operably configured to extend from the cup-shaped member along at least a portion of the lower leg portion of the leg.

6. The apparatus according to claim 3, wherein the cushioning insert means is removably affixable to an interior surface of the tubular portion of the protector apparatus.

7. The apparatus according to claim 1, wherein the first end of the tubular portion has a circumference, in a relaxed configuration, which is substantially greater that the circumference of the second end.

8. The apparatus according to claim 1, wherein the means for enabling resilient expansion of the tubular portion are further configured to permit stretching of the tubular portion in a direction substantially parallel to the longitudinal axis of the tubular portion, and operably configured to promote longitudinal stretching upon said exertion of a stretching force on said tubular portion, so that the amount of longitudinal stretch proximate the first end of the tubular portion having a looser, less compressive degree of elasticity than the amount of longitudinal stretch and associated degree of elasticity proximate to the second end of the tubular portion.

9. The apparatus according to claim 1, wherein the tubular portion includes a substantially bent portion disposed axially between the first and second ends.

10. The apparatus according to claim 1, wherein the tubular portion is configured to insertingly receive and surround the knee region of a leg.

11. The apparatus according to claim 1, wherein the tubular portion is configured to insertingly receive and surround the elbow portion of an arm.

12. A protector apparatus for the facilitated protection of a joint of a human limb, the protector apparatus comprising:

a substantially tubular portion operably configured to insertingly receive and thereafter substantially surround a portion of a human limb, the tubular portion having a first end for orientation of the joint and a second end for orientation below the joint, the tubular portion being open at least one of the first and second ends thereof, the tubular portion having a longitudinal axis;

the tubular portion further including means for enabling resilient stretching of the tubular portion, at least along a circumferential direction on the tubular portion about the longitudinal axis, from an original configuration to one or more stretched configurations, upon exertion of a stretching force on the tubular portion, the means for enabling resilient expansion of the tubular portion further being operably configured to promote circumferential stretching upon said exertion of a stretching force on said tubular portion, the amount of circumferential stretch proximate the first end of the tubular portion having a looser, less compressive degree of elasticity than the amount of circumferential stretch and associated degree of elasticity proximate to the second end of the tubular portion; and cushioning insert means operably disposed along an interior surface of the tubular portion, for facilitated receipt and protection of an exterior surface of a joint of a limb, including a substantially cup-shaped member operably configured to insertingly receive and further cushion a joint of a limb, further including an elongated tongue member, operably emanating downwardly from the cup-shaped member, and operably configured to extend from the cup-shaped member along at least a portion of the lower leg portion of the leg, the elongated tongue member having a width which is substantially less than the width of the cup-shaped member.

13. A protector apparatus for the facilitated protection of a joint of a human limb, the protector apparatus comprising:

a substantially tubular portion operably configured to insertingly receive and thereafter substantially surround a portion of a human limb, the tubular portion having a first upper end for orientation of the joint and a second lower end for orientation proximate the joint, the tubular portion being open at the first upper end thereof, the tubular portion having a longitudinal axis;

the tubular portion further including means for enabling resilient stretching of the tubular portion, at least along a circumferential direction on the tubular portion about the longitudinal axis, from an original configuration to one or more stretched configurations, upon exertion of a stretching force on the tubular portion, the means for enabling resilient expansion of the tubular portion further being operably configured to promote circumferential stretching upon said exertion of a stretching force on said tubular portion, the amount of circumferential stretch proximate the first end of the tubular portion having a looser, less compressive degree of elasticity than the amount of circumferential stretch and associated degree of elasticity proximate to the second end of the tubular portion, and cuff means extending substantially about the respective end of the substantially adjacent tubular portion for facilitated reinforcement of the tubular portion in the regions thereof adjacent the respective end, while accommodating the differentiated degrees of circumferential elasticity between said first and second ends and said cuff means operably disposed substantially adjacent said first upper end of the tubular portion, and possessing a circumferential elasticity no less than that of the portion of the tubular portion proximate thereto.

14. The apparatus according to claim 13, wherein the tubular portion is closed proximate the second, lower end thereof.

* * * * *